(12) United States Patent
Morales et al.

(10) Patent No.: US 9,482,635 B2
(45) Date of Patent: Nov. 1, 2016

(54) GLUCOSE-MEASUREMENT SYSTEMS AND METHODS PRESENTING ICONS

(71) Applicant: Animas Corporation, West Chester, PA (US)

(72) Inventors: Carlos Omar Morales, West Chester, PA (US); Shawn Berven, Philadelphia, PA (US)

(73) Assignee: Animas Corporation, West Chester, PA (US)

( * ) Notice: Subject to any disclaimer, the term of this patent is extended or adjusted under 35 U.S.C. 154(b) by 569 days.

(21) Appl. No.: 13/926,246

(22) Filed: Jun. 25, 2013

(65) Prior Publication Data

US 2014/0374275 A1    Dec. 25, 2014

(51) Int. Cl.
*G01N 27/327*    (2006.01)

(52) U.S. Cl.
CPC ................... *G01N 27/3273* (2013.01)

(58) Field of Classification Search
CPC .................................. G01N 27/3273
See application file for complete search history.

(56) References Cited

U.S. PATENT DOCUMENTS

| | | | |
|---|---|---|---|
| 5,782,805 A | 7/1998 | Meinzer et al. | |
| 6,179,979 B1 | 1/2001 | Hodges et al. | |
| 6,444,115 B1 | 9/2002 | Hodges et al. | |
| 7,276,029 B2 | 10/2007 | Goode, Jr. et al. | |
| 8,163,162 B2 | 4/2012 | Chatelier et al. | |
| 8,287,454 B2 | 10/2012 | Wolpert et al. | |
| 2004/0153257 A1 | 8/2004 | Munk | |
| 2009/0192380 A1 | 7/2009 | Shariati et al. | |
| 2010/0016687 A1 | 1/2010 | Brauker et al. | |
| 2011/0263958 A1 | 10/2011 | Brauker et al. | |
| 2011/0287528 A1 | 11/2011 | Fern et al. | |
| 2013/0137952 A1 | 5/2013 | McCann et al. | |
| 2013/0298063 A1 | 11/2013 | Joy et al. | |

FOREIGN PATENT DOCUMENTS

WO    WO 2011/002904 A2    1/2011

OTHER PUBLICATIONS

David Rodbard, "New Approaches to Display of Self-Monitoring of Blood Glucose Data," Journal of Diabetes Science and Technology, Sep. 2009, pp. 1121-1127, vol. 3, Issue 5.
International Search Report and Written Opinion issued in related International Patent Application No. PCT/US2014/42262, dated Nov. 7, 2014, 18 pages.

*Primary Examiner* — J. Christopher Ball

(57) ABSTRACT

A glucose measurement system includes a display and a biosensor that provides a signal representative of a glucose level of a fluid sample. A processor determines glucose data values and a rate of change of blood glucose using the signal. The processor can determine a state band and a rate band using the values and rate, and display a state icon colored per the state band and a rate icon colored and shaped per the rate band. The processor does not display any other indication of the determined rate of change or of any of the stored glucose data values. The processor can also display a unified icon shaped per the rate of change, with a prevailing color determined using the values. The processor does not display any other indication of the determined rate of change or of any of the stored glucose data values. Corresponding methods are also described.

23 Claims, 8 Drawing Sheets

| | DESC | HOLD | ASC | NORM | WARN | CRIT |
|---|---|---|---|---|---|---|
| | < -5 | [-5, 5] | > 5 | [70,150] | [60,70) + (150,200] | [0,60) + (200,400] |

GLUCOSE-MEASUREMENT SYSTEMS AND METHODS PRESENTING ICONS

TECHNICAL FIELD

This application relates generally to the field of analyte measurement systems and more specifically to an analyte measurement system that presents information from a biosensor on a display as icons.

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and hypoinsulinemia have been associated with a variety of serious symptoms and life-threatening long-term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose (BG) within normal limits. Such glycemic control is achieved by regularly supplying external insulin to the body of the patient to thereby reduce the elevated levels of blood glucose.

External biologic agents such as insulin can be administered as multiple daily injections of a mixture of rapid and intermediate-acting drugs via a hypodermic syringe. Although traditional syringes have at least partly been replaced by insulin pens, the frequent injections are nevertheless very inconvenient for the patient, particularly those who are incapable of reliably self-administering injections. For some patients, substantial improvements in diabetes therapy have been achieved by the development of drug delivery devices, such as pumps, that relieve the patient of the need for syringes or drug pens and the need to administer multiple daily injections. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. An example of a handheld glucose meter/controller unit is the ONETOUCH PING from JOHNSON & JOHNSON.

Drug delivery devices generally provide insulin at a "basal rate," i.e., provide a certain amount of insulin every few minutes in a pre-programmed, daily pattern. Some drug delivery devices also permit the user to specify a "temporary basal," in which the normal daily cycle is altered for a selected length of time. Some drug delivery devices permit the user to manually request that a "bolus," a specified amount of insulin, be delivered at a specified time. For example, before a meal, the user can request a bolus of additional insulin be delivered to process the glucose produced by digestion of the meal. Some drug delivery devices permit the specified amount to be delivered over a period of time rather than all at once; time-extended delivery is referred to as an "extended bolus."

Blood or interstitial glucose monitoring can be used to achieve acceptable glycemic control. The determination of blood glucose concentration can be performed by means of an episodic measuring device, such as a hand-held electronic meter, that receives blood samples on enzyme-based test strips and calculates the blood glucose value based on an electrochemical reaction of the blood and the enzyme. Continuous glucose monitoring (CGM) using a sensor inserted into or implanted in the body can also be used. A combination of a CGM and a drug-delivery device can be used to provide closed loop control of the insulin(s) being infused into the diabetic patients. For convenience, the term "artificial pancreas," as used herein, refers to such a closed-loop system. To allow for closed-loop control of the infused insulins, proportional-integral-derivative ("PID") controllers and model predictive controllers (MPC) have been used. Note that the term "continuous" does not require readings be updated every moment of operation. In practice, CGM generally samples glucose on a regular time scale, e.g., once per five minutes. Closed-loop control updates can be performed, e.g., in the time intervals between glucose measurements.

SUMMARY OF THE DISCLOSURE

Present insulin pumps and CGMs generally provide detailed information about their operations. However, when existing devices are adapted into artificial-pancreas devices, this leads to a previously undiscovered problem of information overload in the patient. Closed-loop controllers involve many variables and can involve significant state tracking, which may not be relevant to the patient. The normal human pancreas, after all, has no user interface. However, present drug-delivery devices are only able to lower blood sugar (by infusing insulin), not to raise it (by infusing glucagon). Therefore, there is a previously-unrecognized need for a user interface that will inform the patient of hypoglycemic excursions (so the patient can take corrective action) but not burden the patient with detail that is not relevant as long as the artificial pancreas is functioning correctly. This need also exists in related medical devices, such as CGMs, and not merely in artificial-pancreas devices.

In one embodiment, therefore, we have devised a glucose measurement system. The system may include the following components:
 a) a biosensor having at least one electrode responsive to an electrochemical reaction between a fluid sample and an enzyme disposed on the at least one electrode, so that the electrochemical reaction of the biosensor provides a signal representative of a glucose level of the fluid sample;
 b) a storage device holding data including definitions of a plurality of state bands of blood glucose and a plurality of rate bands of rate of change of blood glucose;
 c) a processor connected to the biosensor and the storage device and configured to receive successive signals from the biosensor and automatically determine and store corresponding glucose data values, so that the processor determines a rate of change of blood glucose and a corresponding one of the plurality of rate bands using the stored glucose data values and determines one of the plurality of state bands corresponding to a most recent one of the stored glucose data values; and
 d) a display coupled to the processor;
 e) the processor being further configured to display a state icon on the display in a color corresponding to the determined one of the plurality of state bands and to display a rate icon on the display in a color and shape corresponding to the determined one of the plurality of rate bands, so that the processor does not display any other indication of the determined rate of change or of any of the stored glucose data values.

In another embodiment, we have devised a glucose measurement system. The system may include the following components:
  a) a biosensor having at least one electrode responsive to an electrochemical reaction between a fluid sample and an enzyme disposed on the at least one electrode, so that the electrochemical reaction of the biosensor provides a signal representative of a glucose level of the fluid sample;
  b) a storage device holding data including a definition of a color table that maps blood glucose values to color values;
  c) a processor connected to the biosensor and the storage device and configured to receive successive signals from the biosensor and automatically determine and store corresponding glucose data values, so that the processor determines a rate of change of blood glucose using the stored glucose data values; and
  d) a display coupled to the processor,
  the processor being further configured to present on the display a unified icon having:
    i) a shape corresponding to the determined rate of change; and
    ii) a prevailing color determined using the stored color table and a most recent one of the stored glucose data values,
  so that the processor does not display any other indication of the determined rate of change or of any of the stored glucose data values.

In another embodiment, we have devised a method of displaying information about status of blood glucose in a patient. The method can be achieved by automatically performing the following steps using a processor:
  successively receiving a plurality of signals from a biosensor having at least one electrode responsive to an electrochemical reaction between a blood sample and an enzyme disposed on the at least one electrode to provide a signal representative of a glucose level of the blood sample;
  determining a rate of change of glucose level using the received signals representative of respective glucose levels;
  determining an indication whether the determined rate of change of glucose level is in a normal range;
  determining an acuteness and one or more color(s) using the most recent one of the received signals, the determined rate of change, and the determined indication; and
  presenting an icon on a display corresponding to the determined acuteness and color(s), the perimeter of the icon having an at least partially curved segment and, if the determined rate of change is not in the normal range, an opposed acute segment, so that the icon does not include numerical or graphical data of the rate of change or any of the stored glucose data values.

These embodiments exemplary of the present invention advantageously provide display of status information relevant to a user in a readily-comprehensible graphical format. Various embodiments use graphically-simple icons that can be effectively rendered even on small displays, such as those built into insulin pumps. Various embodiments present only the level of detail required for the user to understand his or her medical state, and do not burden the user with information that is not relevant to that state. Various embodiments therefore avoid presenting information that may exacerbate hypochondria, and instead present an interface that provides the user a feeling of stability and control.

Accordingly, in any of the embodiments described earlier, the following features may also be utilized in various combinations with the previously disclosed embodiments. For example, the glucose measurement system can include the storage device holding the data comprising definitions of one or more of a descending, a holding, and an ascending rate band; the processor configured to display in a first shape both the state icon and the rate icon corresponding to the holding band, the processor being further configured so that the first shape substantially points neither upwardly nor downwardly; the processor configured to display the rate icon corresponding to the descending rate band in a shape that points downwardly and to display the rate icon corresponding to the ascending rate band in a shape that points upwardly; the storage device holding the data including definitions of normal, warning, and critical state bands, and normal, descending warning, descending critical, ascending warning, and ascending critical rate bands, and the processor being configured to display the rate icon corresponding to either the descending warning rate band or the descending critical rate band in a shape that points downwardly, display the rate icon corresponding to either the ascending warning rate band or the ascending critical rate band in a shape that points upwardly, display in a shape that substantially points neither upwardly nor downwardly both the state icon and the rate icon corresponding to the normal rate band, display in a first color both the state icon corresponding to the normal state band and the rate icon corresponding to the normal rate band, display in a second color different from the first color both the state icon corresponding to the warning state band and the rate icons corresponding to the descending warning and ascending warning rate bands, and display in a third color different from the first and second colors both the state icon corresponding to the critical state band and the rate icons corresponding to the descending critical and ascending critical rate bands; the storage device holding the data including definitions of normal, low warning, low critical, high warning, and high critical state bands; the processor configured to display the state icon corresponding to either the low warning state band or the low critical state band in a shape that points downwardly, display the state icon corresponding to either the high warning state band or the high critical state band in a shape that points upwardly, and display in a shape that substantially points neither upwardly nor downwardly the state icon corresponding to the normal state band; the storage device holding the including definitions of a normal, moderate-descent, rapid-descent, moderate-ascent, and rapid-ascent rate bands, and the processor configured to select the normal rate band as the determined rate band only if the determined rate of change is within the normal rate band and the determined state band is the normal state band, and otherwise select the moderate-descent, rapid-descent, moderate-ascent, or rapid-ascent rate band as the determined rate band using the stored glucose data values, to display the state icon in a first shape regardless of the determined state band, to display the rate icon corresponding to either the moderate-descent or the rapid-descent rate band in a shape that points downwardly and a color corresponding to the normal state band if the determined state band is the high warning or the high critical state band, or else corresponding to the low warning state band if the determined rate band is the moderate-descent rate band, or else corresponding to the low critical state band if the determined rate band is the rapid-descent rate band, and to display the rate icon corresponding to either the moderate-ascent or the rapid-ascent rate band in a shape that points upwardly and a color corresponding to the normal state band if the determined state band is the low warning or the low critical state band, or else corresponding to the high warning state band if the determined rate band is the moderate-ascent rate band, or else corresponding to the high critical state band if the determined rate band is the rapid-ascent rate band; the processor configured so that neither the state icon nor the rate icon includes numerical or graphical data of the rate of change or any of the stored glucose data values; the storage device holding the data including the definition(s) of at least one of the bands having different limits for increasing values than for decreasing values; or the processor configured to determine when the determined one of the state bands or the determined one of the rate bands changes, and to display the state icon or the rate icon corresponding to the determined band before the change for a selected time period.

In various examples, the glucose management system can include the storage device holding the data of the stored color table including two disjoint ranges of blood glucose with corresponding colors, the processor configured to determine whether the most recent one of the stored glucose data values is within one of the stored ranges, if the most recent one of the stored glucose data values is within one of the stored ranges, the processor configured to select the corresponding color as the prevailing color, and if the most recent one of the stored glucose data values is determined not to be within one of the stored ranges, the processor configured to determine whether the most recent one of the stored glucose data values is between the stored ranges, and if the most recent one of the stored glucose data values is between the stored ranges, the processor configured to interpolate between the corresponding colors according to the most recent one of the stored glucose data values and respective bounds of the stored ranges; the storage device further holding data including a definition of a normal rate band of rate of change of blood glucose and the processor further adapted to determine whether the rate of change is in the normal rate band and to present the unified icon having a shape further corresponding to whether the rate of change is in the normal rate band; the storage device holding the data including the definition of the normal rate band having different limits for increasing values than for decreasing values; the processor configured to display the unified icon having a first shape that substantially points neither upwardly nor downwardly if the rate of change is in the normal rate band, a second shape that substantially points upwardly if the rate of change is outside the normal rate band and positive, and a third shape that substantially points downwardly if the rate of change is outside the normal band and negative; the processor configured so the first shape comprises a circle; the processor configured so that the second and third shapes comprise teardrops, the processor configured to determine an acuteness using the determined rate of change and present the second or third shape having the determined acuteness; the processor configured to interpolate the most recent one of the stored glucose data values and at least two others of the stored glucose data values to provide an interpolated slope as the rate of change and to multiply the interpolated slope by a stored factor to provide the acuteness; the processor configured to display the second and third shapes having a distance between a center of a rounded portion of the teardrop and an end of a pointed portion of the teardrop substantially equal to the determined acuteness; the processor configured so that the unified icon does not include numerical or graphical data of the rate of change or any of the stored glucose data values; or the processor further configured to select a second color using the determined rate of change and to display the unified icon having a color gradient across its area, the color gradient defined by the prevailing color and the second color.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention. For the sake of clarity, like reference numerals herein represent like elements.

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention or the attached claims.

As used herein, the terms "about" or "approximately" for any numerical values or ranges indicate a suitable dimensional tolerance that allows the part or collection of components to function for its intended purpose as described herein. Throughout this disclosure, the terms "patient" and "subject" are used interchangeably. These terms can refer to any human or animal subject and are not intended to limit the systems or methods to human use, although use of the subject invention in a human patient represents a preferred embodiment. Furthermore, in this disclosure, the term "user" can refer to a patient using a glucose measuring device or another person (e.g., a parent or guardian, nursing staff member, home care employee, or other caretaker) using a glucose measuring device. The term "drug" may include hormones, biologically active materials, pharmaceuticals or other chemicals that cause a biological response (e.g., a glycemic response) in the body of a user or patient.

Throughout this disclosure, exemplary blood glucose levels are given in mg/dL. These levels can be divided by 18 to obtain mmol/L. Intervals or other numerical ranges are denoted using parentheses for open endpoints (the value of the endpoint is not included in the interval) and square brackets for closed endpoints (the value of the endpoint is included in the interval), as is common in the mathematical art.

Figure 1:
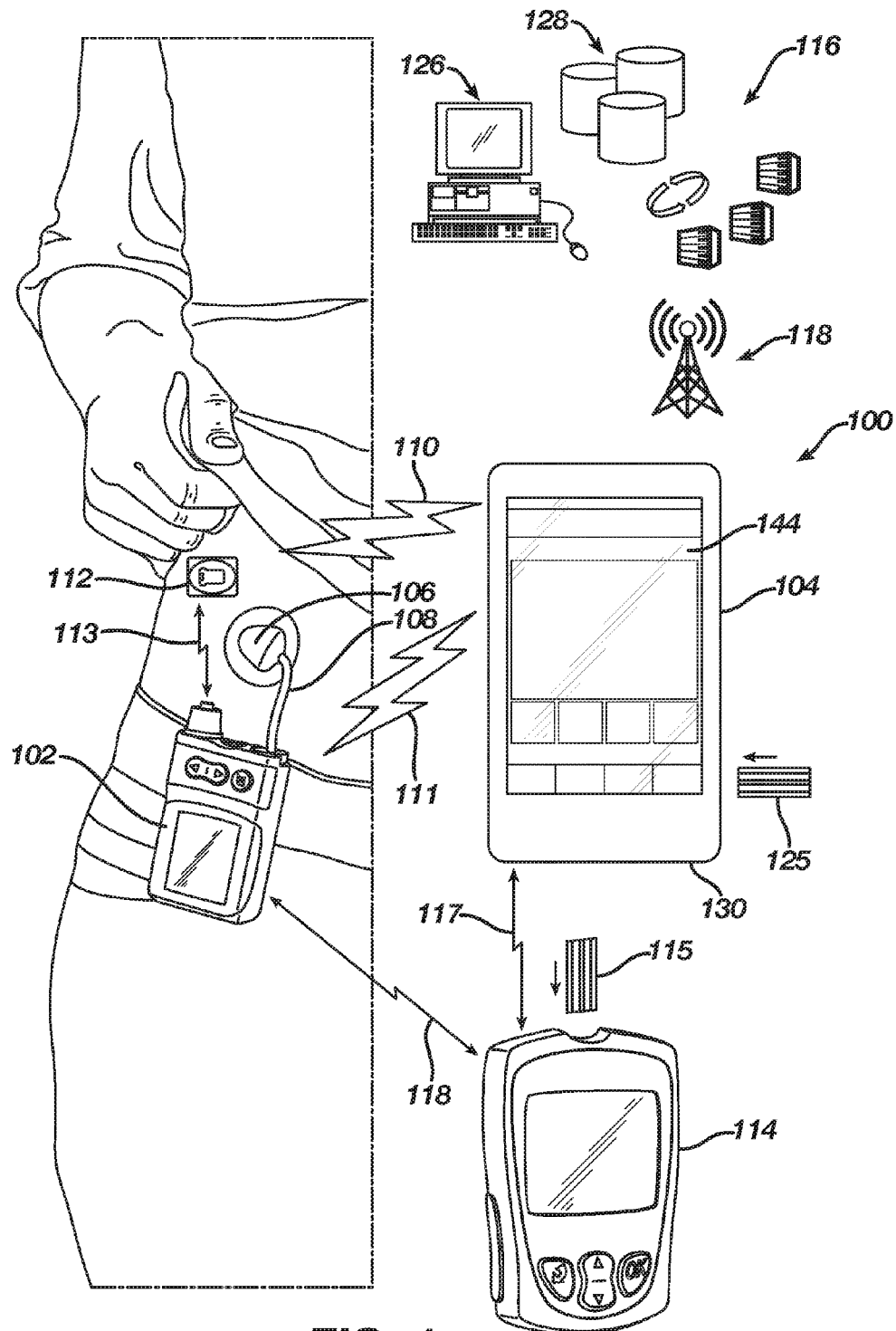
FIG. 1 illustrates an exemplary analyte monitoring and drug delivery system.

FIG. 1 illustrates a glucose-monitoring and drug-delivery system 100, e.g., an artificial pancreas, according to an exemplary embodiment. The drug-delivery system 100 includes a drug delivery device 102 and a controller 104. The drug delivery device 102 is connected to an infusion set 106 via flexible tubing 108. Various embodiments of the invention can also be used with injections via syringe or insulin pen instead of or in addition to infusion via the drug delivery device 102.

The drug delivery device 102 is configured to transmit and receive data to and from the controller 104 by, for example, a radio frequency communications link 111. In one embodiment, the drug delivery device 102 is an insulin infusion device and the controller 104 is a hand-held portable controller. In such an embodiment, data transmitted from the drug delivery device 102 to the controller 104 may include information such as, for example, insulin delivery data, blood glucose information, basal, bolus, insulin to carbohydrates ratio or insulin sensitivity factor. The controller 104 can be configured to include a closed-loop controller that has been programmed to receive continuous glucose readings from a CGM sensor 112 via a radio frequency (RF) communications link 110. Data transmitted from the controller 104 to the drug delivery device 102 may include glucose test results and a food database to allow the drug delivery device 102 to calculate the amount of insulin to be delivered by the drug delivery device 102. Alternatively, the controller 104 may perform basal dosing or bolus calculation and send the results of such calculations to the drug delivery device. A glucose meter 114 (e.g., an episodic blood-glucose meter), alone or in conjunction with the CGM sensor 112, provides data to either or both of the controller 104 and drug delivery device 102, e.g., via a radio frequency (RF) communications link 117. The glucose meter 114 can measure a fluid sample placed on a test strip 115. The two hatched areas on the test strip 115 graphically represent two electrodes, as discussed below and with reference to FIG. 2. The controller 104 can present information and receive commands via a touchscreen 144 or other devices, discussed below with reference to a user interface 330, FIG. 3. The CGM sensor 112 can provide data, e.g., current blood-glucose values, directly to the drug delivery device 102 via a radio frequency (RF) communications link 113.

The controller 104, the drug-delivery device 102, and the CGM sensor 112 can be integrated into multi-function units in any combination. For example, the controller 104 can be integrated with the drug-delivery device 102 to form a combined device with a single housing. Infusion, sensing, and controlling functions can also be integrated into a monolithic artificial pancreas. In various embodiments, the controller 104 is combined with the glucose meter 114 into an integrated monolithic device having a housing 130. Such an integrated monolithic device can receive a test strip 125. In other embodiments, the controller 104 and the glucose meter 114 are two separable devices that are dockable with each other to form an integrated device. Each of the devices 102, 104, and 114 has a suitable micro-controller (not shown for brevity) programmed to carry out various functionalities. Examples of micro-controllers that can be used are discussed below with reference to a processor 386, FIG. 3.

The drug delivery device 102 or the controller 104 can also be configured for bi-directional communication with a network 116 through, for example, a radio frequency communication link 118. One or more server(s) 126 or storage device(s) 128 can be communicatively connected to the controller 104 via the network 116. In an example, the drug delivery device 102 communicates with a personal computer (e.g., the controller 104) via BLUETOOTH low-energy (BLE, also known as BLUETOOTH SMART). The controller 104 and the network 116 can be configured for bi-directional wired communication through, for example, a telephone land based communication network. Controller 104 can include a smartphone, electronic tablet, or personal computer.

The drug delivery device 102 can include any or all of: electronic signal processing components including a central processing unit and memory elements for storing control programs and operation data, a radio frequency module (not shown) for sending and receiving communication signals (e.g., messages) to and from controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, and a drug delivery mechanism (e.g., a drug pump and drive mechanism) for forcing insulin from an insulin reservoir (e.g., a insulin cartridge) through a side port connected via the flexible tubing 108 to an infusion set 106 and into the body of the user.

Various glucose management systems include an episodic glucose sensor (e.g., a glucose meter 114) and an infusion pump. An example of such a system is ONETOUCH PING Glucose Management System manufactured by the Animas Corporation. The "ezBG" feature of this system computes an amount of insulin to be delivered by the infusion pump using the results of an episodic glucose measurement. The pump and meter communicate wirelessly. Another example is the ANIMAS VIBE insulin pump, which communicates with a DEXCOM G4 CGM system manufactured by the DexCom Corporation. Interfaces can be provided to connect these components. Closed-loop control algorithms can be programmed in, e.g., the MATLAB language to regulate the rate of insulin delivery based on the glucose level of the patient, historical glucose measurement and anticipated future glucose trends, and patient specific information.

In an example, the drug delivery device 102 is an insulin pump that communicates directly with the CGM sensor 112 via the link 113. The drug delivery device 102 includes control functions to compute delivery amounts of insulin using blood glucose data from the CGM sensor 112. The controller 104 is a smartphone running an app (downloadable software application) that communicates with the drug delivery device 102 via the link 111 to provide functions for remote operation of the drug delivery device 102 and remote monitoring of blood glucose. The app can perform functions to calculate boluses or adjust insulin delivery amounts.

Figure 2:
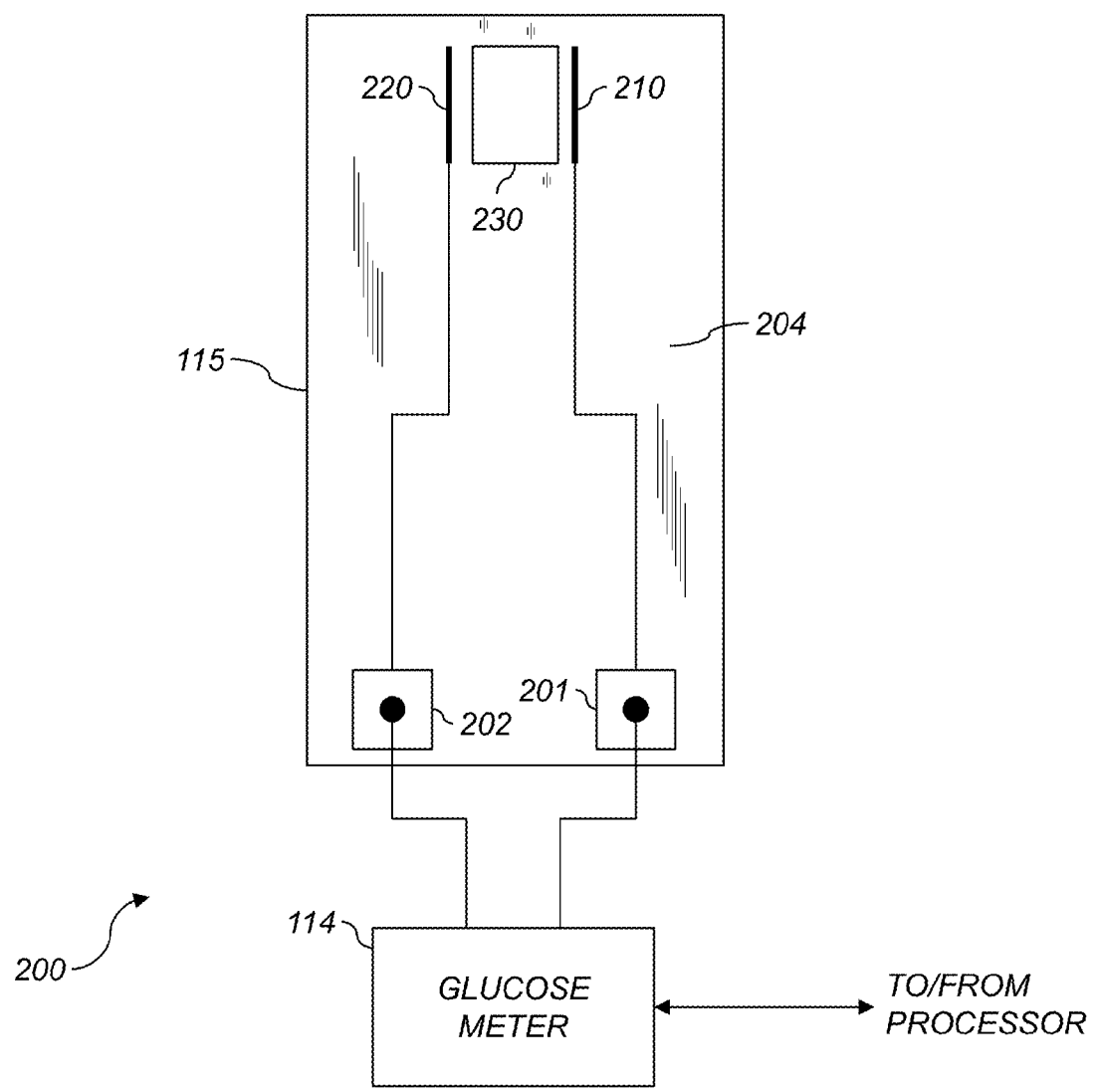
FIG. 2 shows an exemplary biosensor.

FIG. 2 shows an exemplary biosensor 200 for use in an episodic glucose meter. The biosensor 200 is defined by a test strip 115 electrically connected to the glucose meter 114. It should be noted that other configurations of biosensors, e.g., continuous glucose monitors, can also be used with the glucose meter 114 or the controller 104. The test strip 115 is defined by a planar substrate 204 over which are disposed electrodes 210, 220 and electrical contact pads 201, 202. The electrodes 210, 220 can be disposed on opposing sides of a sample-receiving chamber 230, above and below the sample-receiving chamber 230, or in other configurations. The glucose meter 114 can communicate with a processor, e.g., the controller 104, FIG. 1.

In the exemplary test strip 115, the electrode 220 is a working electrode formed by sputtering a Pd coating on a polyester base forming the planar substrate 204. A dry reagent layer is used and includes buffer, mediator, and enzyme, as described herein. The electrode 210 is a reference electrode formed by sputtering an Au coating on the polyester base forming the planar substrate 204. The electrical contact pads 201, 202 connect to the electrodes 210, 220, respectively, and permit applying or detecting electrical signals across the sample-receiving chamber 230 between the electrodes 210, 220. The sample-receiving chamber 230 can have a volume ranging from, e.g., about 0.1 microliters to about 5 microliters. Various enzymes in the sample-receiving chamber 230 can assist in transducing the analyte (e.g., glucose) in the fluid sample (e.g., blood) into a current, potential, or other quantity that can be measured electrically. Exemplary enzymes include glucose oxidase, glucose dehydrogenase (GDH) based on a pyrroloquinoline quinone co-factor, and GDH based on a nicotinamide adenine dinucleotide co-factor.

In use, top ends of the electrodes 210, 220 are in contact with an electrolyte phase (not shown), which is a free-flowing fluid phase (e.g., a blood sample) disposed between the electrodes 210, 220. An enzyme, e.g., glucose oxidase, can cover the electrolyte phase. Depending on the state of the test strip 200, the electrode 210 can be a working electrode and the electrode 220 can be a counter electrode. In an example using glucose oxidase, a current is produced at the working electrode (and flows through the circuitry to the counter electrode). That current is representative of the concentration of glucose in the subject's body. The glucose meter 114 can measure the current through the electrodes 210, 220 to determine the glucose level of the fluid sample in the sample-receiving chamber 230. Exemplary glucose sensors and associated components are shown and described in U.S. Pat. Nos. 6,179,979, 8,163,162, and 6,444,115, which are incorporated by reference herein in their entireties.

In another example of a biosensor 200, an exemplary CGM sensor 112 utilizes amperometric electrochemical sensor technology to measure an analyte. The CGM sensor 112 includes three electrodes operably connected to the sensor electronics and covered by a sensing membrane and a biointerface membrane, which are attached by a clip. The top ends of the electrodes are in contact with an electrolyte phase (not shown), which is a free-flowing fluid phase disposed between the sensing membrane and the electrodes. The sensing membrane may include an enzyme, e.g., analyte oxidase, which covers the electrolyte phase.

The $H_2O_2$ produced from the analyte oxidase reaction further reacts at the surface of working electrode and produces two protons (2H+), two electrons (2e−), and one oxygen molecule ($O_2$). A potentiostat is used to measure the electrochemical reaction(s) at the electrode(s) by applying a constant potential between the working and reference electrodes to produce a current value. The current that is produced at the working electrode (and flows through the circuitry to the counter electrode) is proportional to the diffusional flux of $H_2O_2$. Accordingly, a raw signal may be produced that is representative of the concentration of analyte in the user's body, and therefore may be utilized to estimate a meaningful analyte value. Details of the sensor and associated components are shown and described in U.S. Pat. No. 7,276,029, which is incorporated by reference herein. The CGM sensor 112 can measure analyte levels in, e.g., interstitial fluid.

Figure 3:
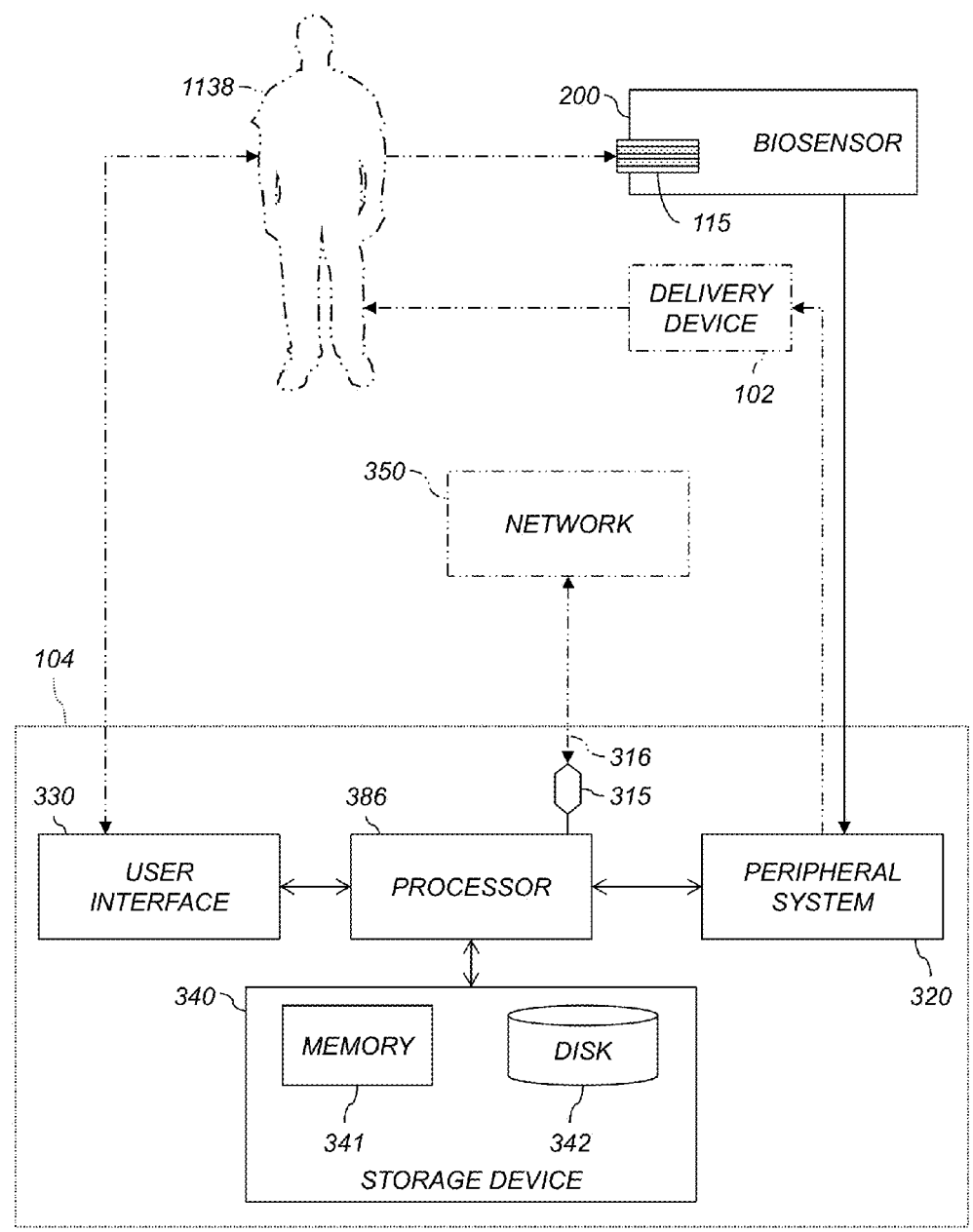
FIG. 3 shows an exemplary system for the measurement of blood glucose, and related components.

FIG. 3 shows an exemplary glucose measurement system, including data-processing components for analyzing data and performing other analyses and functions described herein, and related components. A subject 1138, a network 350, and a drug-delivery device 102 are not part of the system, but are shown for purposes of context. The controller 104 can communicate with the biosensor 200 (that can receive the test strip 115), the drug-delivery device 102, or the network 350. The processor 386 in the controller 104 can receive glucose data from the biosensor 200 (a CGM sensor, or an episodic sensor using the test strip 115) and provide control signals to the drug-delivery device 102 to deliver insulin to the subject 1138.

The controller 104 can also include a peripheral system 320, a user interface 330, and a storage device 340 communicatively connected to the processor 386. The processor 386 includes one or more data processor(s) that implement processes of various embodiments described herein. A "data processor" is a device for processing data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise. The phrase "communicatively connected" includes any type of connection, wired or wireless, between devices, data processors, or programs in which data can be communicated. Subsystems such as the peripheral system 320, the user interface 330, and the storage device 340 are shown separately from the processor 386 but can be stored completely or partially within the processor 386.

The storage device 340 includes or is communicatively connected with one or more tangible non-transitory computer-readable storage medium(s) configured to store information, including the information needed to execute processes according to various embodiments. The term "device" does not require that the storage device 340 include only one piece of hardware that stores data. A "tangible non-transitory computer-readable storage medium" as used herein refers to any non-transitory device or article of manufacture that participates in storing instructions which may be provided to the processor 386 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM).

Embodiments of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct the processor 386 to perform a particular series of operational steps when loaded, thereby implementing functions or acts specified herein.

In an example, the storage device 340 includes a memory 341, e.g., a random-access memory, and a disk 342, e.g., a tangible computer-readable storage device such as a hard drive or a solid-state flash drive. Computer program instructions are read into the memory 341 from the disk 342, or a wireless, wired, optical fiber, or other connection. The processor 386 then executes one or more sequences of the computer program instructions loaded into the memory 341, as a result performing process steps and other processing described herein. In this way, the processor 386 carries out a computer implemented process that provides for technical effects of converting glucose to glucose data and presenting that data graphically. For example, blocks of the flowchart illustrations or block diagrams herein, and combinations of those, can be implemented by computer program instructions. The memory 341 can also store data used by running programs.

Program code to carry out methods described herein can execute entirely on a single processor 386 or on multiple communicatively-connected processors 386. For example, code can execute wholly or partly on a user's computer and wholly or partly on a remote computer, e.g., a server. The remote computer can be connected to the user's computer through the network 350. The user's computer or the remote computer can be non-portable computers, such as conventional desktop personal computers (PCs), or can be portable computers such as tablets, cellular telephones, smartphones, or laptops.

The peripheral system 320 can include one or more devices configured to provide digital content records or other data to the processor 386. For example, the biosensor 200 can be connected to the processor 386 via the peripheral system 320, e.g., using a BLUETOOTH SMART or other wireless link. The biosensor 200 can also be directly connected to the processor 386. The peripheral system 320 can also include digital still cameras, digital video cameras, cellular phones, or other data processors. The peripheral system 320 can also include one or more bus bridge(s), e.g., to communicatively connect devices having USB, FIREWIRE, RS-232, or other interfaces to the processor 386. The processor 386, upon receipt of data from a device in the peripheral system 320, can store that data in the storage device 340.

The processor 386 is communicatively connected to the user interface 330. The user interface 330 can include a mouse, a keyboard, another computer (connected, e.g., via a network or a null-modem cable), a microphone and speech processor or other device(s) for receiving voice commands, a camera and image processor or other device(s) for receiving visual commands, e.g., gestures, or any device or combination of devices from which data is input to the processor 386. In this regard and although the peripheral system 320 is shown separately from the user interface 330, the peripheral system 320 can be included as part of the user interface 330. In at least one embodiment, the user interface 330 can be operated by the subject 1138.

The user interface 330 also can include a display device, a touchscreen, a processor-accessible memory, or any device or combination of devices to which data is output by the processor 386. In this regard, if the user interface 330 includes a processor-accessible memory, such memory can be part of the storage device 340 even though the user interface 330 and the storage device 340 are shown separately in FIG. 3. For example, the user interface 330 can include one or more touchscreen(s), speaker(s), buzzer(s), vibrator(s), button(s), jack(s), plug(s), or network connection(s), or a switch or switches.

In various embodiments, the processor 386 is communicatively connected to a communication interface 315 that is coupled via a network link 316 to the network 350. For example, the communication interface 315 can be a WIFI or BLUETOOTH SMART wireless transceiver and the network link 316 can be a radio-frequency (RF) communications channel. As another example, the communication interface 315 can be a network card to provide a data communication connection to a compatible local-area network (LAN), e.g., an Ethernet LAN, or wide-area network (WAN). The communication interface 315 sends and receives electrical, electromagnetic or optical signals that carry digital data streams representing various types of information across the network link 316 to the network 350. The network link 316 can be connected to the network 350 via a switch, gateway, hub, router, or other networking device.

The processor 386 can send messages and receive data, including program code, to and from the network 350 via the network link 316 and the communication interface 315. For example, requested code for an application program (e.g., a JAVA applet) can be stored on a tangible non-volatile computer-readable storage medium connected to the network 350. A network server (not shown) can retrieve the code from the medium and transmit it via the network 350 to the communication interface 315. The received code can be executed by the processor 386 as it is received, or stored in the storage device 340 for later execution.

The processor 386 can be configured to operate in an open-loop mode. In this operating mode, the system behaves like a traditional, open-loop controlled insulin pump. Insulin is delivered according to a patient-set basal rate profile and patient-calculated meal and correction boluses. CGM data can be recorded and displayed for patient information, but are not used for automated insulin calculations. Similar functions are provided by, e.g., the ANIMAS VIBE insulin pump with a DEXCOM G4 CGM system.

The processor 386 can also be configured to operate in a closed-loop mode. In this operating mode, the processor 386 commands the drug delivery device 102 to deliver the patient's pre-set basal rates modulated, if necessary, by a predictive closed-loop control algorithm that uses as one of its inputs the glucose values communicated by the biosensor 200. Glucose values can be received from the biosensor 200, e.g., every five minutes. This permits reducing the probability of hypoglycemic excursions beyond a low glucose limit or hyperglycemic excursions beyond a high glucose limit. Low and high glucose limits can be defined by a healthcare provider (HCP) or patient. Users can calculate meal and correction boluses. The processor 386 can be configured to provide a bolus calculator via the user interface 330 to assist users in determining bolus insulin amounts. The closed-loop control algorithm can take these manual boluses into account in forming an Insulin On Board (IOB) estimate, and then can use the IOB estimate to determine how much additional insulin is required to process a detected level of blood glucose.

The processor 386 can also be configured to operate in a maintenance mode in which low-level control of the drug delivery device 102 is provided via the user interface 330. Control of other functions not typically accessed by patients can also be provided. This mode can permit testing the controller 104, the drug delivery device 102, or the biosensor 200 during manufacturing or, e.g., when the controller 104 and the biosensor 200 require service.

Figure 4:
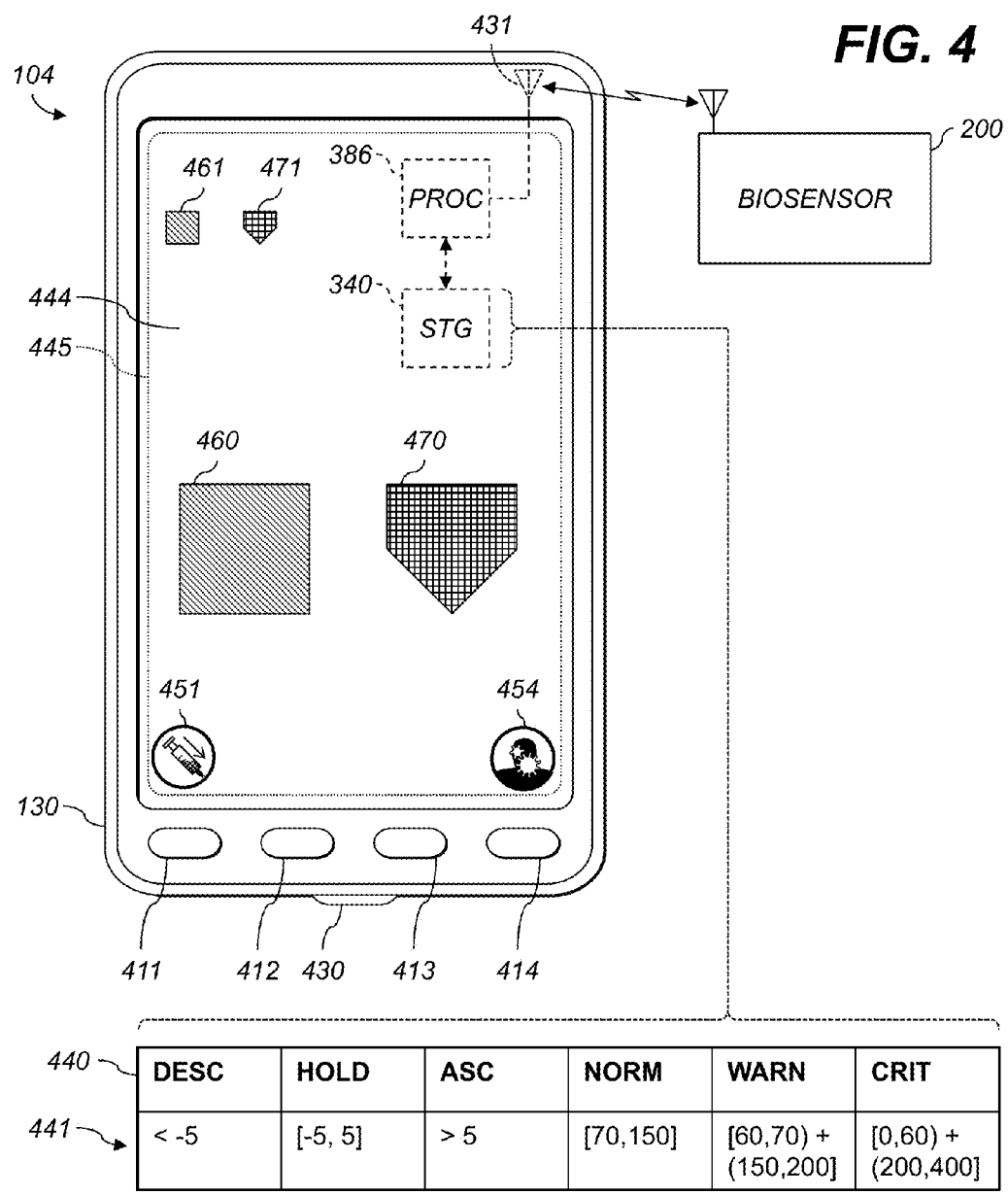
FIG. 4 shows an exemplary glucose measurement system.

FIG. 4 shows an exemplary glucose measurement system, including a controller 104 having a housing 130. The system, and other glucose measurement systems described herein, can also be referred to as "decision-support systems" since they provide information to the subject 1138, FIG. 3, may use in the process of deciding how to manage blood glucose levels. The controller 104 can include a smartphone. Disposed within the housing 130 are the processor 386, the storage device 340, and an antenna 431. The processor 386 communicates wirelessly with the biosensor 200 via the antenna 431. Disposed on the housing 130 is a docking port 430. Also arranged in the housing 130 are the elements of the user interface 330, including a display 444, which is coupled, as is well known to those skilled in the art, to the processor 386, and optionally one or more input device(s).

The processor 386 is coupled, as is well known to those skilled in the art, to the user interface 330 to provide graphic output and receive input. Examples of input devices include a joystick or a directional-pad pointing device (not shown), a switch (not shown), and soft keys 411, 412, 413, 414. In one example, the input device is a touch sensor 445 operatively arranged with respect to the display 444 to form a touchscreen. In the example shown, the soft keys 411, 414 are input devices. The soft key 411 requests a bolus be infused via a drug-delivery device, represented graphically by a soft-key label 451. The soft key 414 invokes a user-settings menu or dialog, represented graphically by a soft-key label 454.

In at least one embodiment, the controller 104 is integrated with the drug-delivery device 102. The display 444 and the soft keys 411, 412, 413, 414 make up an interface with which the patient interacts with the drug delivery device 102. The user interface 330 can also permit user control of functions not described herein of the drug delivery device 102. The display 444 can be, e.g., an organic light-emitting diode (OLED) display, a liquid-crystal display (LCD), or another type of electronic display. The display 444 can include pixels arranged in a matrix of rows and columns. The display 444 can include specific shaped elements, e.g., larger than 3 mm$^2$, that selectively illuminate, or that selectively reflect or transmit light substantially uniformly, across their area. Examples of such elements are found in some electroluminescent displays on automobile radios, and on automotive LCDs that display icons or text messages defined by the design of the LCD panel rather than by selective activation of pixels in a matrix. A common example of a large-element display is a seven-segment display that uses seven large elements, selectively illuminated, to display the digits 0-9. The display 444 can include shaped elements corresponding to shapes and colors of a state icon 460, a rate icon 470, or a unified icon 560, as described herein.

The storage device 340 holds data including definitions of a plurality of state bands of blood glucose and a plurality of rate bands of rate of change of blood glucose. The data can be hard-coded in a stored program, or deposited in a table consulted by the processor 386 while executing a stored program. Bands can include hysteresis; examples are discussed below. Exemplary data are shown by an inset 440, discussed below.

The processor 386 is communicatively connected to the biosensor 200 and the storage device 340. The processor 386 is configured to receive successive signals from the biosensor 200 and automatically determine and store corresponding glucose data values. The processor 386 can apply averaging, smoothing, hysteresis, or other known techniques in determining the glucose data values from the successive signals. The processor 386 determines a rate of change of blood glucose. This can be done, e.g., by differencing or curve-fitting and differentiation. An example of linear curve-fitting and differentiation (slope extraction) is given below. The processor 386 then determines a corresponding one of the plurality of rate bands using the stored glucose data values and one of the plurality of state bands corresponding to a most recent one of the stored glucose data values. This is discussed below.

The processor 386 is configured to display a state icon 460 on the display 444 in a color corresponding to the determined one of the plurality of state bands. The processor 386 is also configured to display a rate icon 470 on the display in a color and shape corresponding to the determined one of the plurality of rate bands. The processor 386 is configured so that it does not display any other indication of the determined rate of change or of any of the stored glucose data values. For example, the state icon 460 and the rate icon 470 do not show any numbers or graphs. In the example shown, the state icon 460 is a green square and the rate icon 470 is a yellow downward-pointing arrow. In various embodiments, such as that shown, neither the state icon nor the rate icon includes numerical or graphical data of the rate of change or any of the stored glucose data values. Only information about the bands is provided in this example. This provides the user a clean, simple, readily comprehensible status display.

Figure 5:
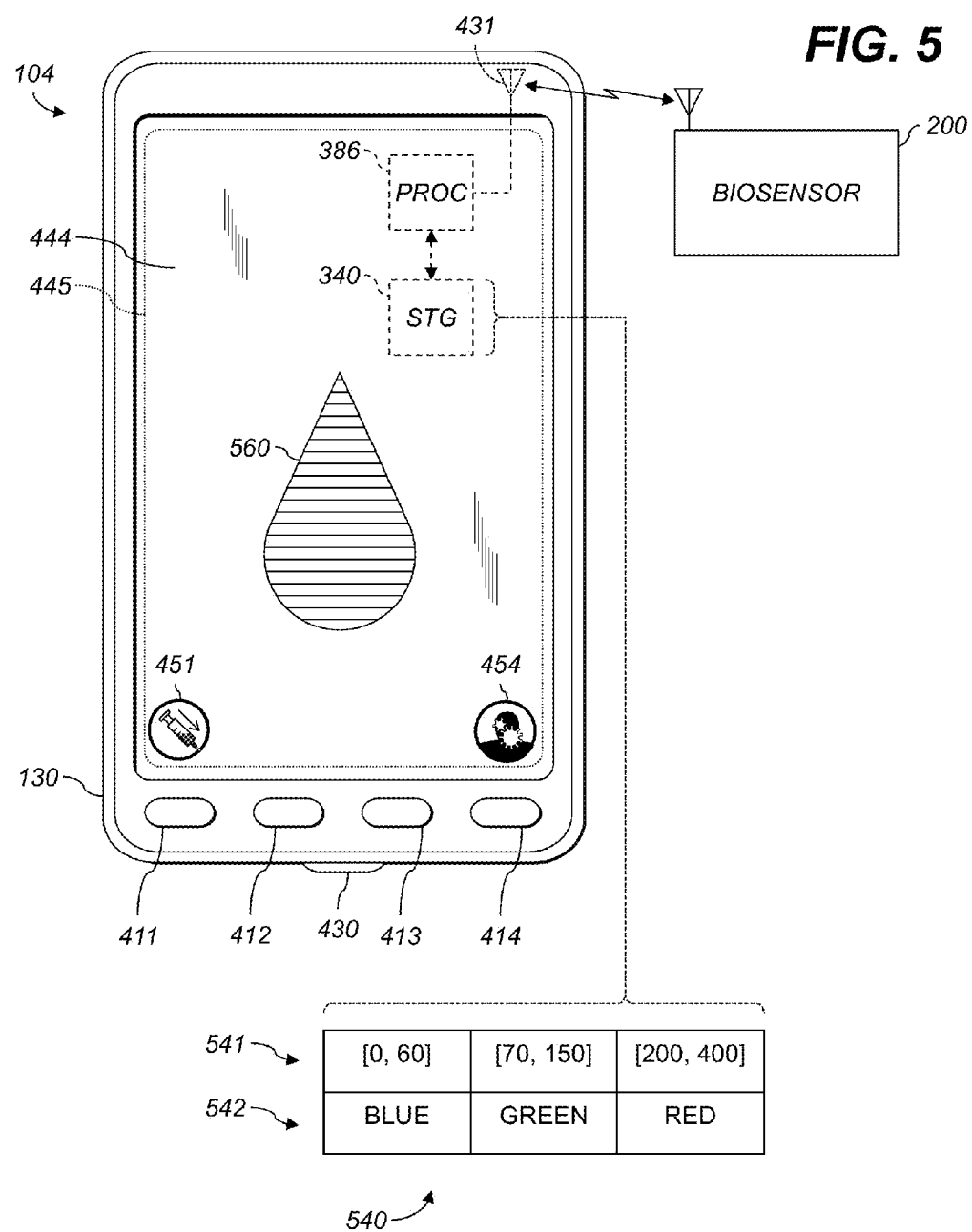
FIG. 5 shows an exemplary glucose measurement system.

Throughout the following discussion, the term "icons" refers to any or all of the state icon 460, the rate icon 470, and a unified icon 560, FIG. 5. The icons are graphical presentations designed to be perceived by the user rapidly and as a whole. The processor 386 displays each of the icons to convey information to the user, e.g., to inform the user of the determined state band via the state icon 460.

The normal human visual system (HVS) can typically resolve features subtending at least one minute of arc (arcmin). For example, a pattern of alternating equal-width black and white lines can be perceived as such a pattern when each of the lines is at least 1 arcmin wide. If the lines are narrower than 1 arcmin, the pattern is perceived as a gray field rather than as a pattern of lines. An example of a 1-arcmin pattern is found in the sans-serif letter "E" optotype occupying the top row of a Snellen optometric test chart. This optotype has horizontal strokes 1 arcmin high and spaces between the strokes 1 arcmin high when viewed with the three parallel strokes pointing to the right at a distance of 20 feet (for U.S. charts) or 6 m (for international charts). A person with 20/20 vision viewing a U.S. chart at 20 feet can distinguish the horizontal lines and spaces in the "E." In general, when designing icons to be presented by the processor 386 as described herein, a desired visual acuity of a reference observer can be selected. For general use, a visual acuity of 1 arcmin can be selected. For specific situations, other visual acuities can be selected. For example, for icons designed to be viewed in foggy or smoky rooms that blur light from the display 444, a visual acuity of 2 arcmin can be selected, i.e., the icons will be sized to be readily perceptible by a user that can only reliably resolve 2-arcmin-wide features due to the blurring. Such icons can be, e.g., twice as large (e.g., in pixels) as icons designed for a reference observer with a 1-arcmin visual acuity.

Given the limited visual acuity of the HVS, in various embodiments, each of the icons is designed and sized so that the shape of the perimeter of that one of the icons can be clearly perceived by the reference observer at a selected viewing distance (e.g., at arm's length, or 1 foot, 2 feet, 0.5 m, 1 m, or another selected distance). Each of the icons is further designed so that any and all information to be conveyed by that one of the icons is clearly perceptible by the reference observer viewing that one of the icons at the selected viewing distance. Any of the icons can include features too small to be readily perceptible by the reference observer at the selected viewing distance, provided those features are not intended to convey information. For example, any of the icons can include black or white areas that simulate the appearance of a raised shape or a glossy plastic shape reflecting a light source. These black or white areas are not intended to convey information, so can be smaller than would be readily perceptible. Color gradients or textures can also be used in the icons. These gradients or textures can be designed to be large enough to be readily perceptible if they are intended to carry information. Gradients or textures not intended to carry information can be designed to be any size; it is not required that they be readily perceptible at the selected viewing distance.

In an example, the rate icon 470 is designed to subtend more than 1 arcmin in order for a reference observer with a visual acuity of 1 arcmin (a "one-arcmin observer") to distinguish an upward-pointing arrow from a downward-pointing arrow. Selecting 5 arcmin as the angle to subtend so that the shape of the perimeter of the rate icon 470 will be readily perceptible to the one-arcmin observer, and selecting the selected viewing distance of 1 m, the exemplary rate icon 470 is at least 0.145 cm (=1 m×tan$^{-1}$ 5 arcmin) tall, which is at least six pixels in height on an exemplary 96 dot-per-inch (dpi) display. In general, if the reference observer is viewing one of the icons from a distance smaller than the selected viewing distance, the one of the icons will subtend more than the angle subtended at the selected viewing distance. Therefore, icons designed to be readily perceptible at the selected viewing distance are also readily perceptible at distances closer than the selected viewing distance, with the possible exception of distances so short that the eye cannot adequately focus on the icons. Depending on the shape and color of the icons, however, they may be readily perceptible even when viewed out-of-focus.

The sizes of the icons can be selected according to the usage model. For example, icons designed to be readily perceptible at a quick glance can have a larger actual size than icons designed to be perceptible only when the eyes focus on them. In an example, the state icon 460 and the rate icon 460 are placed on a "home" screen of the controller 104. The state icon 460 and the rate icon 470 are thus displayed except when the user specifically requests a different display, e.g., by pressing the soft key 414 to invoke a user-settings screen. The display 444 in this example is 96 dpi. The state icon 460 and the rate icon 470, in order for the user to be able to see them at a glance, can be designed to be 60×60 pixels on the home screen (subtending 55 arcmin at a viewing distance of 1 m). In order for the subject 1138 to be able to monitor his or her blood glucose while interacting with the user-settings screen, an exemplary user-settings screen can include a state icon 461 and a rate icon 471. The state icon 461 and the rate icon 471 are 25% of the size of the state icon 460 and the rate icon 470, i.e., 15×15 pixels in this example (subtending 14 arcmin at 1 m). In this way, BG information is readily available on the user-settings screen should the subject 1138 choose to focus on the icons 461, 471. However, the BG information occupies a relatively small percentage of the screen, leaving room for user-settings information and input controls on the display 444. The user will generally be focusing on the display 444 while interacting with the user-settings screen, so (in this example) it is not necessary that the state icon 461 or the rate icon 471 be readily perceptible at a quick glance.

So that the icons can be readily perceived as a whole, in various examples, each of the icons subtends at most 10°, or at most 2° (131 pixels at 96 dpi and 1 m distance), of the user's field of vision at the selected viewing distance. In various examples, colors are applied to the icons so that, once the shapes of the icons are perceptible, the colors are also perceptible. In an example, icons that may be colored yellow have actual sizes (e.g., in pixels) larger than icons that will only be colored red or green, since desaturated yellows can be difficult to perceive when they subtend only small angles of the field of view.

The inset 440 shows exemplary data stored in the storage device 340. A data record 441 in the data includes definitions of descending ("DESC"), holding ("HOLD"), and ascending ("ASC") rate bands. In this example, the descending rate band is a rate of change of BG more negative than −5 mg/dL/min. The hold rate band is a rate of change on [−5,5] mg/dL/min. The ascending rate band is a rate of change greater than +5 mg/dL/min. In this way, the holding rate band is similar to a dead band between determinations that BG is increasing and determination that BG is decreasing. Throughout this disclosure, references to what the data "define" refer to what the data includes a definition of.

Various shapes can be used for purposes of displaying the state icon 460 and the rate icon 470. In an example, the processor 386 is configured to display in a first shape both the state icon 460 and the rate icon 470 corresponding to the holding band. The processor 386 is also configured so that the first shape substantially points neither upwardly nor downwardly. For example, the first shape can be a circle, square, diamond, a sideways-pointing triangle, such as an equilateral triangle with one edge being oriented vertically, or an isosceles triangle with the non-equal side being oriented vertically. Alternatively, the shape can be one of many polygons as long as the polygon generally points neither upwardly or downwardly.

In various embodiments, the processor 386 is configured to display the rate icon corresponding to the descending rate band in a shape that points downwardly, e.g., a downward-pointing arrow or triangle. According to one example, the processor 386 is configured to display the rate icon corresponding to the ascending rate band in a shape that points upwardly. The icon can also be oppositely configured if desired in order to indicate an action the user may desire to take. For example, an upward-pointing arrow can mean either "blood glucose is going up" or "increase your blood glucose" (e.g., by eating fruit).

In an example, the data in the storage device 340 define normal (in the inset 440, "NORM"), warning ("WARN"), and critical ("CRIT") state bands. In this example, the normal band is [70,150] mg/dL. The warning band includes both [60,70) (a low warning band) and (150,200] (a high warning band). The critical band includes both [0,60) (a low critical band) and (200,400] (a high critical band). In the example, the upper limit of the high critical band can be set according to the maximum BG reading the biosensor 200 is capable of providing. For example, some BG meters can measure BG values as high as 700 mg/dL, or as high as 800 mg/dL, or higher than 800 mg/dL.

In various embodiments, the data in the storage device 340 can also define normal, descending warning, descending critical, ascending warning, and ascending critical rate bands. For example, the (−∞,−5) descending band can be divided into (−∞,−10) for descending critical and [−10-5) for descending warning. Similarly, ascending warning can be (5,10] and ascending critical can be (10,∞).

In various embodiments, the processor 386 is configured to display the rate icon 470 corresponding to either the descending warning rate band or the descending critical rate band in a shape that points downwardly. The processor 386 is further configured, in these embodiments, to display the rate icon 470 corresponding to either the ascending warning rate band or the ascending critical rate band in a shape that points upwardly. The processor 386 is further configured to display in a shape, e.g., that substantially points neither upwardly nor downwardly (e.g., a circle, square, or diamond) both the state icon 460 (regardless of the determined state band) and the rate icon 470 corresponding to the normal rate band. Using the same shape for "steady" in both the state icon 460 and the rate icon 470 can reduce the cognitive burden to the user of understanding the information being presented.

The processor 386 is also configured to select colors of the state icon 460 and the rate icon 470 in various embodiments. The processor 386 can be configured to display in a first color both the state icon 460 corresponding to the normal state band and the rate icon 470 corresponding to the normal rate band. For example, when BG is in-range and steady, both the state icon 460 and the rate icon 470 can be displayed as green squares. Using the same color for "normal" in both the state icon 460 and the rate icon 470 can reduce the cognitive burden to the user of understanding the information presented. The processor 386 can thus be configured to display both the state icon 460 corresponding to the warning state band and the rate icons 470 corresponding to the descending warning and ascending warning rate bands in a second color different from the first color. The processor 386 can be further configured to display in a third color, different from the first and second colors, both the state icon 460 corresponding to the critical state band and the rate icons 470 corresponding to the descending critical and ascending critical rate bands. The use of different first, second, and third colors in this way can provide a readily-comprehensible display of band information.

In various embodiments, the storage device 340 holds data including definitions of normal (e.g., [70,150]), low warning (e.g., [60,70)), low critical (e.g., [0,60)), high warning (e.g., (150,200]), and high critical (e.g., (200,400]) state bands. The processor 386 can be configured to display the state icon 460 corresponding to either the low warning state band or the low critical state band in a shape that points downwardly. Using shapes for the state icon 460 can advantageously provide information to, e.g., colorblind users or users viewing displays with significant color distortion, such as some liquid-crystal displays viewed off-axis. The processor 386 can correspondingly be configured to display the state icon 460 corresponding to either the high warning state band or the high critical state band in a shape that points upwardly, and to display the state icon 460 corresponding to the normal state band in a shape that substantially points neither upwardly nor downwardly.

In some systems, the direction of a trend and an indication of whether the trend is beneficial or detrimental is sufficient information for a user to take meaningful action. In various embodiments, therefore, the data in the storage device 340 further define normal, moderate-descent, rapid-descent, moderate-ascent, and rapid-ascent rate bands, e.g., respectively similar to the normal, descending warning, descending critical, ascending warning, and ascending critical rate bands discussed previously. The processor 386 is configured to select the normal rate band as the determined rate band, but only if the determined rate of change is within the normal rate band and the determined state band is the normal state band. Otherwise, the processor 386 is configured to select the moderate-descent, rapid-descent, moderate-ascent, or rapid-ascent rate band as the determined rate band using the stored glucose data values. In many diabetic patients, especially those with Type 1 diabetes, BG can change continuously and sometimes erratically or unpredictably. The processor 386 is configured to display the rate icon 470 only when BG variations are small (e.g., within the normal rate band naturally or due to the infusion of insulin by an artificial pancreas) and within the normal state band. In these embodiments, when BG is not within the normal state band, BG will be changing for better or for worse. Accordingly, the processor 386 selects the appropriate ascent or descent rate band.

Continuing this example, the processor 386 is configured to display the state icon 460 in a first shape regardless of the determined state band. The processor 386 can display the state icon 460 in a color that corresponds to the determined state band (e.g., red, yellow, or green). The processor 386 is configured to display the rate icon 470 corresponding to either the moderate-descent or the rapid-descent rate band in a shape that points downwardly and to display the rate icon 470 corresponding to either the moderate-ascent or the rapid-ascent rate band in a shape that points upwardly.

For moderate-descent or rapid-descent rate bands, the processor 386 can display the rate icon 470 in a color corresponding to the normal state band if the determined state band is the high warning or the high critical state band, corresponding to the low warning state band if the determined state band is the normal state band, or corresponding to the low critical state if the determined state band is the low warning or the low critical state band. For moderate or rapid-ascent rate bands, the processor 386 can display the rate icon 470 in a color corresponding to the normal state band if the determined state band is the low warning or the low critical state band, corresponding to the high warning state band if the determined state band is the normal state band, or corresponding to the high critical state if the determined state band is the high warning or the high critical state band.

In various embodiments, the processor 386 is configured to display the rate icon corresponding to either the moderate-descent or the rapid-descent rate band in a shape that points downwardly and a color corresponding to the normal state band if the determined state band is the high warning or the high critical state band, or else corresponding to the low warning state band if the determined rate band is the moderate-descent rate band, or else corresponding to the low critical state band if the determined rate band is the rapid-descent rate band. The processor 386 is further configured, in these embodiments, to display the rate icon corresponding to either the moderate-ascent or the rapid-ascent rate band in a shape that points upwardly and a color corresponding to the normal state band if the determined state band is the low warning or the low critical state band, or else corresponding to the high warning state band if the determined rate band is the moderate-ascent rate band, or else corresponding to the high critical state band if the determined rate band is the rapid-ascent rate band. In an example of such embodiments, the processor 386 presents to the user, e.g., two green squares if BG is being maintained in range. If BG is out of range or is changing noticeably (i.e., rate of change outside the hold band), the user sees the state icon 460 indicating, e.g., "how bad is it now?", and the rate icon 470 indicating, e.g., "is it getting better or worse?". If the rate icon 470 has a color corresponding to the normal state band, e.g., green, BG is moving back into range whether it is currently too high or too low.

Figure 6:
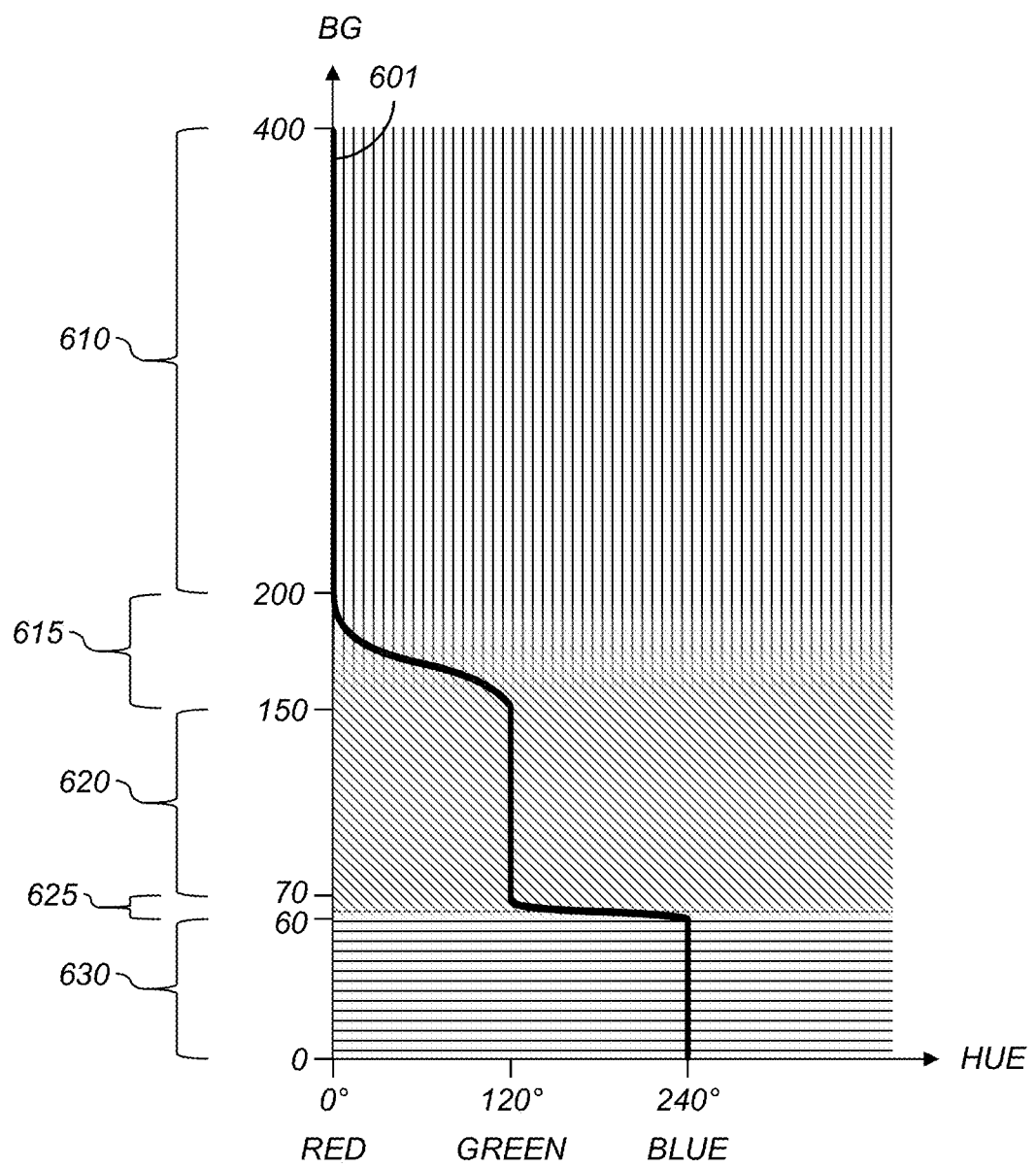
FIG. 6 is a graphical representation of an exemplary color table.

In various embodiments, the definitions of the one or more of the bands as stored in the data, e.g., in the storage device 340, have different limits for increasing values than for decreasing values. In another example, the bands are disjoint, i.e., the definitions are such that no value of BG is in more than one band. In yet another example, the bands are disjoint and not abutting, e.g., intermediate ranges 615, 625, FIG. 6, are nonempty. In this latter example, the processor 386 can be configured to change the determined band not when BG (or rate of change, and likewise throughout) leaves a currently-determined band, but only when BG (rate) enters a different band. This provides hysteresis between bands. Hysteresis reduces the probability of "flicker," i.e., numerous icon changes occurring in quick succession. Flicker can occur when values are near the edges of bands and, in some systems, can lead the user to feel less certain about the operation of the device than may be desirable. Hysteresis is not required in some systems, depending on, e.g., whether values tend to remain near band edges for extended periods of time. In the example shown in FIG. 6, if BG is fluctuating in the interval [140,190], the determined band will be a range 620. The processor 386 will not change the determined band as BG increases and decreases through 150, reducing flicker. The processor 386 will change the determined band to a range 610 only when BG increases through 200, in this example.

Still referring to FIG. 4, in various embodiments, the processor 386 is configured to reduce flicker without regard to the limits of the bands. The processor 386 is configured to determine when the determined one of the state bands or the determined one of the rate bands changes, and to display the state icon 460 or the rate icon 470 corresponding to the determined band before the change for a selected time period. The selected time period can be defined in clock time (e.g., seconds) or in BG-reading or sensor-update cycles.

FIG. 5 shows an exemplary glucose measurement system. A biosensor 200 has at least one electrode responsive to an electrochemical reaction between a fluid sample and an enzyme disposed on the at least one electrode, so that the electrochemical reaction of the biosensor provides a signal representative of a glucose level of the fluid sample. Examples of the biosensor 200 are discussed above. A display 444 is coupled, as is well known to those skilled in the art, to the processor 386.

The storage device 340 holds data including a definition of a color table that maps blood glucose values to color values. An example is shown in an inset 540. For each range in a dataset 541, there is a corresponding color in a dataset 542. In this particular example, the range [70,150] of blood glucose values corresponds to the color green, the range [0,60] to blue, and the range [200,400] to red. The upper limit (e.g., 400) can be selected based on the peak level of glucose the biosensor 200 is capable of detecting.

The processor 386 is connected to the biosensor 200 and the storage device 340. The processor 386 is configured to receive successive signals from the biosensor 200 and automatically determine and store corresponding glucose data values. This determining of values can involve, e.g., averaging or hysteresis, as discussed above. The processor 386 is also configured to determine a rate of change of blood glucose using the stored glucose data values.

The processor 386 is configured to present a unified icon 560 on the display 444. Various attributes of the unified icon 560, e.g., visibility to the reference observer, are discussed above with reference to FIG. 4. The unified icon 560 has a shape corresponding to the determined rate of change. In this example, the determined rate of change is positive (BG is increasing), so the shape of the unified icon 560 is a teardrop pointing upwardly, as viewed by the user. As discussed above, the shape of the unified icon 560 can either indicate status (e.g., upward=high glucose) or suggest action (e.g., upward=raise glucose). In various embodiments, the unified icon 560 does not include numerical or graphical data of the rate of change or any of the stored glucose data values. In various examples, the processor 386 is configured to determine an acuteness using the determined rate of change and present the unified icon 560 as a shape having the determined acuteness. The unified icon 560 is designed so that, as acuteness changes, the impression of a change in blood glucose presented by the unified icon 560 changes. Examples of acuteness are discussed below with reference to FIG. 7.

The unified icon 560 also has a prevailing color determined using the stored color table and a most recent one of the stored glucose data values. As discussed above, the processor 386 can present the unified icon 560 so that the prevailing color is readily apparent, e.g., to the reference observer viewing the unified icon 560 at a selected viewing distance. In this example, the prevailing color is blue, and, as shown, the entire icon (except for the border) is displayed blue. This presentation indicates that the current level is low, since blue corresponds to a BG range of [0,60] mg/dL. The processor 386 does not display any other indication of the determined rate of change or of any of the stored glucose data values. Although the prevailing color can define the initial or predominant impression of the unified icon 560 perceived by the user, other colors can also be applied to the unified icon 560. An example of functional coloration is discussed below with reference to FIG. 8. Colors other than the predominant color can also be applied to the unified icon 560 to provide improved graphical appearance (e.g., glossy highlights) or to permit ready visual discrimination of the shape (e.g., a black border).

FIG. 6 is a graphical representation of an exemplary color table. The ordinate shows blood glucose (BG) in mg/dL. The abscissa shows hue in degrees, for a curve 601 (red=0°, green=120°, blue=240°). The hatched background represents the color for each BG value; the width of the hatched background is not significant for purposes discussed herein. In this example, the data of the stored color table include three disjoint ranges 610, 620, 630 of blood glucose with corresponding colors. Any number ≥2 of disjoint ranges can be used. The processor 386, FIG. 5, is configured to determine whether the most recent one of the stored glucose data values is within one of the stored ranges 610, 620, 630. If the data value is within one of the stored ranges 610, 620, 630, the processor 386 selects the corresponding color as the prevailing color.

In this example, BG is limited to the interval [0,400], e.g., by physical limitations of the CGM sensor 112, FIG. 1. If the most recent one of the stored glucose data values is not within one of the stored ranges 610, 620, 630, therefore, that value is within one of two intermediate ranges 615, 625. Any number ≥1 of intermediate ranges can be used. In general, it is not required that BG be limited to a particular interval, or that the two or more stored ranges (e.g., the stored ranges 610, 620, 630) cover any specific ranges of BG values. The processor 386 determines whether the most recent stored glucose data value is between the stored ranges, e.g., in the intermediate range 615 between the ranges 610, 620. If so, e.g., that data value is in the intermediate range 615, the processor 386 is configured to interpolate between the corresponding colors (e.g., red and green), according to the most recent one of the stored glucose data values and respective bounds of the stored ranges (e.g., the ranges 610, 620). This interpolation can be seen in the curve 601, which shows smooth changes in hue across the intermediate ranges 615, 625. Interpolation can be linear, S-curve, or otherwise, and can be performed in RGB, HSV, or other color spaces. Another exemplary CGM sensor 112 limits BG to the interval [40,400].

Figure 7:
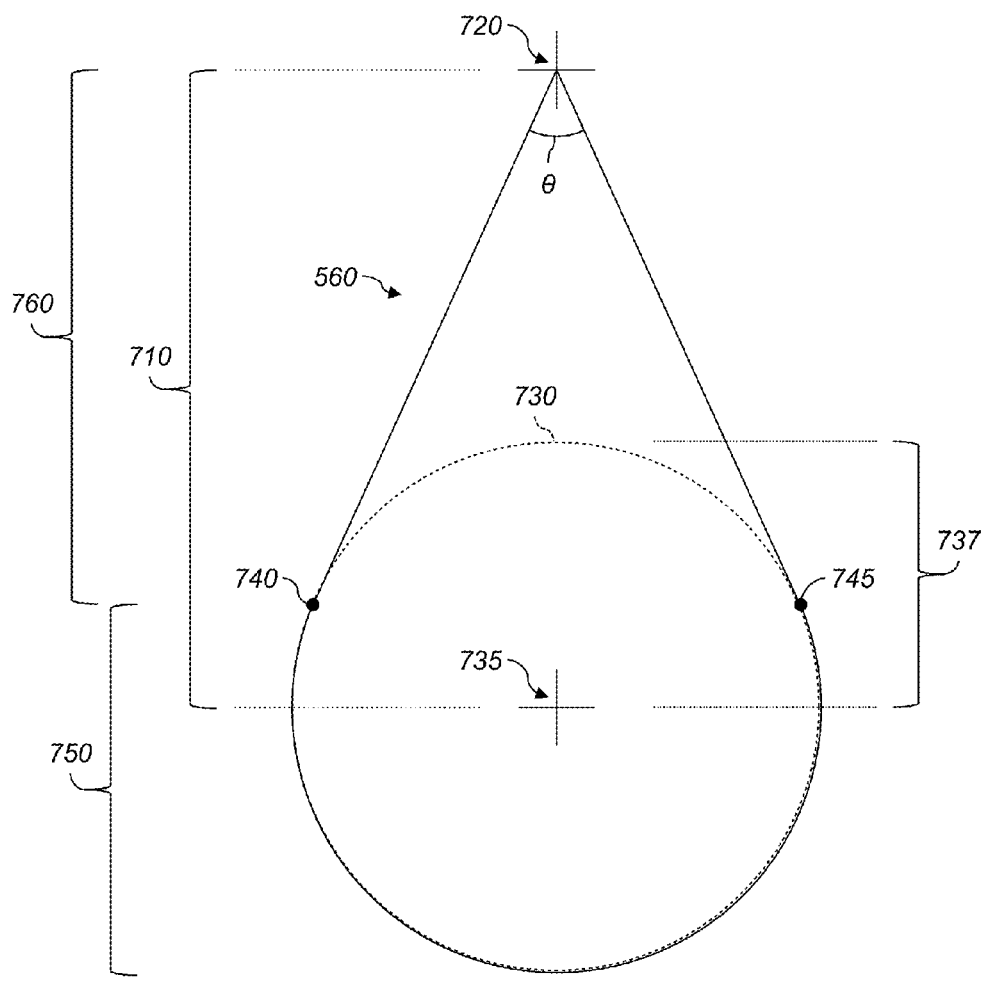
FIGS. 7 and 8 are graphical representations of exemplary unified icons.

FIG. 7 shows an exemplary shape of a unified icon 560, namely a teardrop shape, and illustrates exemplary computations the processor 386 performs to determine the exemplary shape. The processor 386 determines a circle 730 with a selected center 735 and a selected radius 737, e.g., a center and a radius stored in the storage device 340. The processor 386 then determines an acuteness 710. In this example, the acuteness 710 is the distance from the center 735 to the apex of the teardrop at a point 720 determined by the processor 386. The processor 386 then determines two tangent line segments between the point 720 and the circle 730. The tangent points of these line segments are shown as the two points 740, 745. Tangents to a circle, e.g., the circle 730, can be determined as is well-known in trigonometry. The processor 386 then determines that the shape includes the area of the circle 730 and the additional area enclosed by a triangle with vertices at the points 720, 740, 745. The perimeter of the resulting shape has an arcuate segment 750 and a polyline segment 760. Determinations described herein, as well as other shape determinations throughout this disclosure, can be performed by the processor 386 operating on vector data, raster data, or a combination of vector and raster data.

In various examples, the acuteness determined by the processor 386 is an angle, e.g., angle θ, or a value correlated with an angle, e.g., the acuteness 710. The processor 386 can be configured to determine the acuteness 710 using the determined rate of change of blood glucose.

In another example, the unified icon 560 includes a segment of a superellipse including points (x, y) where $|x|^n+|y|^n=1$, n>0, those points then optionally scaled to a desired size, or translated to a desired orientation, of the unified icon 560. For positive rates of change, the unified icon 60 can include the superellipse points satisfying y>0, e.g., instead of the polyline segment 760. For negative rates of change, the superellipse points satisfying y<0 can be used. In this example, the acuteness is the value of n.

For example, when n=2, the superellipse is a semicircle, so the unified icon 560 is a circle. As n decreases from 2 towards 1, the superellipse becomes more pointed at the top, bottom, left, and right. Accordingly, the unified icon 560 including the segment of the superellipse becomes more pointed either up or down according to the rate of change. At n=1, the superellipse is a diamond, so the unified icon 560 includes a right angle pointing either upwardly or downwardly. As n further decreases toward 0, the angle decreases toward 0, so the points of the unified icon 560 become increasingly pointed (acute). Note than n>2 can also be used; as n increases, the superellipse becomes more and more square-shaped, until it is a square at n=∞. Note that elliptical, superelliptical, and rectangular shapes can be produced by dividing x and y by desired constants as is known in the mathematical art.

In various embodiments, the storage device 340, FIG. 5, holds data including a definition of a normal rate band of rate of change of blood glucose. The processor 386, FIG. 5, is further adapted to determine whether the rate of change is in the normal rate band and to present the unified icon having a shape dependent upon whether the rate of change is in the normal rate band. For example, if the determined acuteness 710 is less than the radius 737, the rate of change is in the normal rate band and the shape is a circle rather than a teardrop. It will be readily apparent that other shapes can be used. In an example, the shape is a square if the rate of change is in the normal rate band and a triangle otherwise (e.g., pointing upwardly for ascending; pointing downwardly for descending). In general, the processor 386 can be configured to display the unified icon 560 having, e.g., a first shape that substantially points neither upwardly nor downwardly if the rate of change is in the normal rate band, a second shape that substantially points upwardly if the rate of change is outside the normal rate band and positive, and a third shape that substantially points downwardly if the rate of change is outside the normal band and negative. The first, second, or third shapes can be convex or not, and can be simply-connected or not. The first shape can be a circle or a substantially-circular shape, e.g., as shown here. The second and third shapes can be teardrops or substantially teardrop shapes, as discussed above. Any teardrop shape displayed by the processor 386 can have a distance between a center of a rounded portion of the teardrop and an end of a pointed portion of the teardrop substantially equal to the determined acuteness. In general, the processor 386 can present the second or third shape having the determined acuteness.

In various embodiments, hysteresis is used, e.g., as described above. For example, the definition of the normal rate band can have different limits for increasing values than for decreasing values. In at least one example, the processor 386 is configured to interpolate the most recent one of the stored glucose data values and at least two others of the stored glucose data values to provide an interpolated slope as the rate of change and to multiply the interpolated slope by a stored factor to provide the acuteness. The stored factor can be selected based on the size or resolution of the display 444, FIG. 5.

Figure 8:
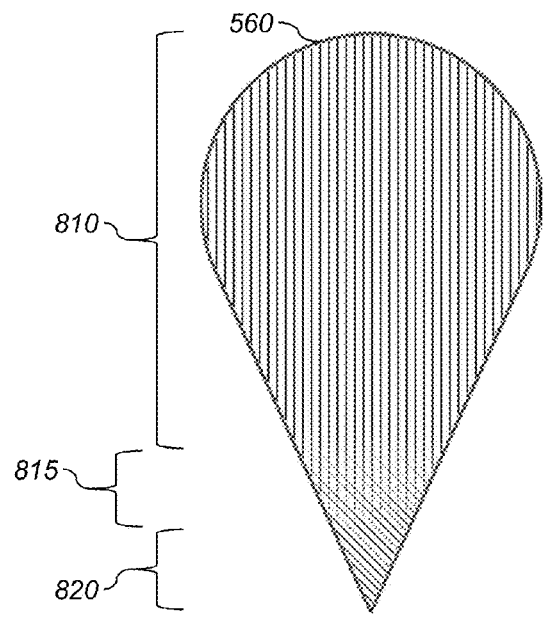

FIG. 8 is a graphical representation of an exemplary unified icon 560 shaped as a downward-pointing teardrop and having a color gradient across its area. The unified icon 560 has a red portion 810, a green portion 820, and a gradient portion 815 that blends from red to green. In this example, the prevailing color is red, indicating that the most recent of the blood glucose values is in a hyperglycemic range. To produce this visual appearance, the processor 386 is configured to select a second color (e.g., green) using the determined rate of change. Examples of second colors can include red for increasing or blue for decreasing, or green for improvement and red for disimprovement. The processor 386 is configured to display the unified icon 560 having a color gradient across its area, the color gradient defined by the prevailing color (e.g., red) and the second color (e.g., green). The gradient portion 815 can occupy the full area of the unified icon 560, or less than the full area.

Figure 9:
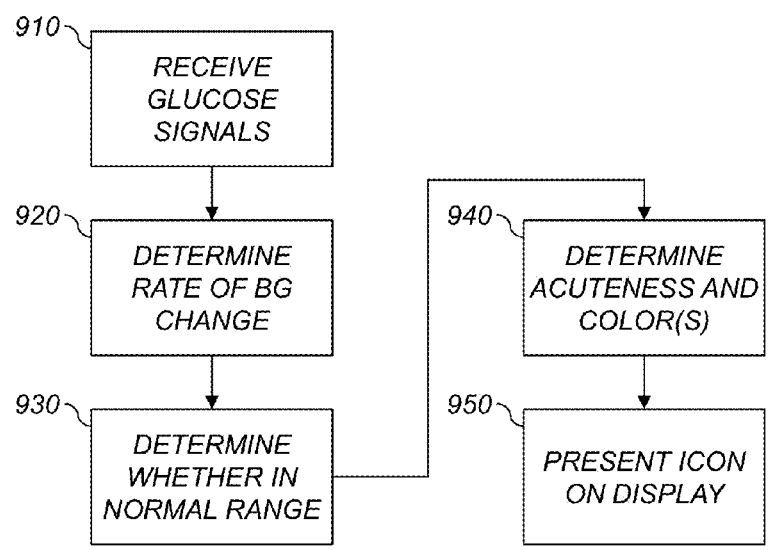
FIG. 9 is a flowchart illustrating an exemplary method for displaying information relating to status of blood glucose in a patient.

FIG. 9 is an exemplary flowchart illustrating an exemplary method for displaying information about status of blood glucose in a patient. The method includes automatically performing steps described below using the processor 386 or another processor or controller. The steps can be performed in any order except when otherwise specified, or when data from an earlier step is used in a later step. For purposes of this exemplary method, processing begins with step 910. For clarity of explanation, reference is herein made to various components shown in FIGS. 1-5 that can carry out or participate in the steps of the exemplary method. It should be noted, however, that other components can be used; that is, the exemplary method is not limited to being carried out by the identified components.

In step 910, a plurality of signals are successively received from a biosensor 200 having at least one electrode responsive to an electrochemical reaction between a blood sample and an enzyme disposed on the at least one electrode to provide a signal representative of a glucose level of the blood sample.

In step 920, a rate of change of glucose level is determined using the received signals representative of respective glucose levels. This can be done, e.g., by fitting a line to the most recently received n glucose levels (e.g., n=3 or n=10) and taking the slope of the fitted line as the rate of change.

In step 930, an indication whether the determined rate of change of glucose level is in a normal range is determined. This can be done by comparing the determined rate of change to a normal rate band stored in the storage device 340.

In step 940, an acuteness and one or more color(s) are determined using the most recent one of the received signals, the determined rate of change, and the determined indication. Various examples of such determinations are discussed above with reference to FIGS. 4-8.

In step 950, an icon is presented on a display. The icon, e.g., the unified icon 560, corresponds to the determined acuteness and color(s). For example, the icon can be colored in a single prevailing color or a two-color gradient. The perimeter of the icon has an at least partially curved segment (e.g., the arcuate segment 750, FIG. 7). If the determined rate of change is not in the normal range, the perimeter of the icon also has an opposed acute segment (e.g., the polyline segment 760, FIG. 7). The presented icon does not include numerical or graphical data of the rate of change or any of the stored glucose data values.

In other embodiments, after step 920, one of a plurality of state bands corresponding to a most recent one of the stored glucose data values is determined. One of a plurality of rate bands corresponding to the determined rate of change is also determined using the stored glucose data values. A state icon is then displayed on the display in a color corresponding to the determined one of the plurality of state bands. A rate icon is displayed on the display in a color and shape corresponding to the determined one of the plurality of rate bands. No other indication of the determined rate of change or of any of the stored glucose data values is displayed.

In view of the foregoing, embodiments of the invention provide improved displays of band information determined from blood glucose data. Various features described herein provide ways of displaying information in a way readily comprehensible by users. A technical effect of the biosensor and the processing performed by the processor is to convert glucose levels in a blood sample to data and communicate those data graphically outside the particular computing device that performed the conversion, e.g., to a human user.

PARTS LIST FOR FIGS. 1-9

100 system
102 drug delivery device
104 controller
106 infusion set
108 flexible tubing
110, 111 radio frequency communications links
112 CGM sensor
113 communications link
114 glucose meter
115 test strip
116 network
117, 118 radio frequency communications links
125 test strip
126 server
128 storage device
130 housing
144 touchscreen
200 biosensor
201, 202 electrical contact pads
204 planar substrate
210, 220 electrodes
230 sample-receiving chamber
315 communication interface
316 network link
320 peripheral system
330 user interface
340 storage device
341 memory
342 disk
350 network
386 processor
411,412,413,414 soft keys
430 docking port
431 antenna
440 inset
441 data record
444 display
445 touch sensor
451, 454 soft-key labels
460, 461 state icons
470, 471 rate icons
540 inset
541 dataset
542 dataset
560 unified icon
601 curve
610 range
615 intermediate range
620 range
625 intermediate range
630 range
710 acuteness
720 point
730 circle
735 center
737 radius
740, 745 points
750 arcuate segment
760 polyline segment
810 red portion
815 gradient portion
820 green portion
910, 920, 930, 940, 950 steps
1138 subject While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Separate references to "an embodiment" or "particular embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted. To the extent there are variations of the invention that are within the spirit of the disclosure or are equivalent to the inventions found in the claims, it is the intent that this patent will cover those variations as well.

What is claimed is:

1. A glucose measurement system comprising:
    a) a biosensor having at least one electrode responsive to an electrochemical reaction between a fluid sample and an enzyme disposed on the at least one electrode, so that the electrochemical reaction of the biosensor provides a signal representative of a glucose level of the fluid sample;
    b) a storage device holding data including definitions of a plurality of state bands of blood glucose, and a plurality of rate bands of rate of change of blood glucose;
    c) a processor connected to the biosensor and the storage device and configured to receive successive signals from the biosensor and automatically determine and store corresponding glucose data values, so that the processor determines a rate of change of blood glucose and a corresponding one of the plurality of rate bands using the stored glucose data values and determines one of the plurality of state bands corresponding to a most recent one of the stored glucose data values; and
    d) a display coupled to the processor;
    e) the processor being further configured to display a state icon on the display in a color corresponding to the determined one of the plurality of state bands and to display a rate icon on the display in a color and shape corresponding to the determined one of the plurality of rate bands, in which the color of the state icon and the color of the rate icon extends over the entirety of each respective icon, so that the processor does not display any other indication of the determined rate of change or of any of the stored glucose data values and wherein neither the state icon nor the rate icon comprise numbers or graphs.

2. The system according to claim 1, the data comprising definitions of one of more of a descending, a holding, and an ascending rate band.

3. The system according to claim 2, the processor being configured to display in a first shape both the state icon and the rate icon corresponding to the holding band, the processor being further configured so that the first shape substantially points neither upwardly nor downwardly.

4. The system according to claim 2, the processor being configured to display the rate icon corresponding to the descending rate band in a shape that points downwardly and to display the rate icon corresponding to the ascending rate band in a shape that points upwardly.

5. The system according to claim 1, the data comprising definitions of a normal, a warning, and a critical state band, and of a normal, a descending warning, a descending critical, an ascending warning, and an ascending critical rate band, and the processor being configured to:
    a) display the rate icon corresponding to either the descending warning rate band or the descending critical rate band in a shape that points downwardly;
    b) display the rate icon corresponding to either the ascending warning rate band or the ascending critical rate band in a shape that points upwardly;
    c) display in a shape that substantially points neither upwardly nor downwardly both the state icon and the rate icon corresponding to the normal rate band;
    d) display in a first color both the state icon corresponding to the normal state band and the rate icon corresponding to the normal rate band;
    e) display in a second color different from the first color both the state icon corresponding to the warning state band and the rate icons corresponding to the descending warning and ascending warning rate bands; and
    f) display in a third color different from the first and second colors both the state icon corresponding to the critical state band and the rate icons corresponding to the descending critical and ascending critical rate bands.

6. The system according to claim 1, the data comprising definitions of a normal, a low warning, a low critical, a high warning, and a high critical state band.

7. The system according to claim 6, the processor being configured to:
    a) display the state icon corresponding to either the low warning state band or the low critical state band in a shape that points downwardly;
    b) display the state icon corresponding to either the high warning state band or the high critical state band in a shape that points upwardly; and
    c) display in a shape that substantially points neither upwardly nor downwardly the state icon corresponding to the normal state band.

8. The system according to claim 6, the data further comprising definitions of a normal, a moderate-descent, a rapid-descent, a moderate-ascent, and a rapid-ascent rate band and the processor being configured to:
    a) select the normal rate band as the determined rate band only if the determined rate of change is within the normal rate band and the determined state band is the normal state band, and otherwise select the moderate-descent, rapid-descent, moderate-ascent, or rapid-ascent rate band as the determined rate band using the stored glucose data values;
    b) display the state icon in a first shape regardless of the determined state band;
    c) display the rate icon corresponding to either the moderate-descent or the rapid-descent rate band in a shape that points downwardly and a color:
        i) corresponding to the normal state band if the determined state band is the high warning or the high critical state band; or else
        ii) corresponding to the low warning state band if the determined ate band is the moderate-descent rate band; or else
        iii) corresponding to the low critical state band if the determined rate band is the rapid-descent rate band; and
    d) display the rate icon corresponding to either the moderate-ascent or the rapid-ascent rate band in a shape that points upwardly and a color:
        i) corresponding to the normal state band if the determined state band is the low warning or the low critical state band; or else
        ii) corresponding to the high warning state band if the determined rate band is the moderate-ascent rate band; or else
        iii) corresponding to the high critical state band if the determined rate band is the rapid-ascent rate band.

9. The system according to claim 1, wherein neither the state icon nor the rate icon includes numerical or graphical data of the rate of change or any of the stored glucose data values.

10. The system according to claim 1, the definition(s) of at least one of the bands in the data having different limits for increasing values than for decreasing values.

11. The system according to claim 1, the processor further configured to determine when the determined one of the state bands or the determined one of the rate bands changes, and to display the state icon or the rate icon corresponding to the determined band before the change for a selected time period.

12. A glucose measurement system comprising:
a) a biosensor having at least one electrode responsive to an electrochemical reaction between a fluid sample and an enzyme disposed on the at least one electrode, so that the electrochemical reaction of the biosensor provides a signal representative of a glucose level of the fluid sample;
b) a storage device holding data including a definition of a color table that maps blood glucose values to color values;
c) a processor connected to the biosensor and the storage device and configured to receive successive signals from the biosensor and automatically determine and store corresponding glucose data values, so that the processor determines a rate of change of blood glucose using the stored glucose data values; and
d) a display coupled to the processor,
the processor being further configured to present on the display a unified icon having:
 i) a shape corresponding to the determined rate of change; and
 ii) a prevailing color determined using the stored color table and a most recent one of the stored glucose data values,
so that the processor does not display any other indication of the determined rate of change or of any of the stored glucose data values.

13. The system according to claim 12, the data of the stored color table including two disjoint ranges of blood glucose with corresponding colors,
the processor being configured to determine whether the most recent one of the stored glucose data values is within one of the stored ranges,
if the most recent one of the stored glucose data values is within one of the stored ranges, the processor configured to select the corresponding color as the prevailing color, and
if the most recent one of the stored glucose data values is determined not to be within one of the stored ranges, the processor configured to determine whether the most recent one of the stored glucose data values is between the stored ranges, and if the most recent one of the stored glucose data values is between the stored ranges, the processor configured to interpolate between the corresponding colors according to the most recent one of the stored glucose data values and respective bounds of the stored ranges.

14. The system according to claim 12, the storage device further holding data including a definition of a normal rate band of rate of change of blood glucose and the processor further adapted to determine whether the rate of change is in the normal rate band and to present the unified icon having a shape further corresponding to whether the rate of change is in the normal rate band.

15. The system according to claim 14, the definition of the normal rate band in the data having different limits for increasing values than for decreasing values.

16. The system according to claim 14, the processor configured to display the unified icon having a first shape that substantially points neither upwardly nor downwardly if the rate of change is in the normal rate band, a second shape that substantially points upwardly if the rate of change is outside the normal rate band and positive, and a third shape that substantially points downwardly if the rate of change is outside the normal band and negative.

17. The system according to claim 16, the first shape substantially comprising a circle.

18. The system according to claim 16, the second and third shapes substantially comprising teardrops, the processor being configured to determine an acuteness using the determined rate of change and present the second or third shape having the determined acuteness.

19. The system according to claim 18, the processor being configured to interpolate the most recent one of the stored glucose data values and at least two others of the stored glucose data values to provide an interpolated slope as the rate of change and to multiply the interpolated slope by a stored factor to provide the acuteness.

20. The system according to claim 19, the processor configured to display the second and third shapes having a distance between a center of a rounded portion of the teardrop and an end of a pointed portion of the teardrop substantially equal to the determined acuteness.

21. The system according to claim 12, wherein the unified icon does not include numerical or graphical data of the rate of change or any of the stored glucose data values.

22. The system according to claim 12, the processor further configured to select a second color using the determined rate of change and to display the unified icon having a color gradient across its area, the color gradient defined by the prevailing color and the second color.

23. A method of displaying information about status of blood glucose in a patient, the method comprising automatically performing the following steps using a processor:
successively receiving a plurality of signals from a biosensor having at least one electrode responsive to an electrochemical reaction between a blood sample and an enzyme disposed on the at least one electrode to provide a signal representative of a glucose level of the blood sample;
determining a rate of change of glucose level using the received signals representative of respective glucose levels;
determining an indication whether the determined rate of change of glucose level is in a normal range;
determining an acuteness and one or more color(s) using the most recent one of the received signals, the determined rate of change, and the determined indication; and
presenting an icon on a display corresponding to the determined acuteness and color(s), the perimeter of the icon having an at least partially curved segment and, if the determined rate of change is not in the normal range, an opposed acute segment, so that the icon does not include numerical or graphical data of the rate of change or any of the stored glucose data values.

* * * * *